United States Patent [19]
Nakamura et al.

[11] Patent Number: 5,286,905
[45] Date of Patent: Feb. 15, 1994

[54] PROCESS FOR PRODUCING BIGUANIDE DERIVATIVE

[75] Inventors: Kazufumi Nakamura; Masahiro Nishii; Ryoichi Adachi; Masatoshi Uemura; Ichiro Nasuno; Izumi Terada; Takashi Mitsuyama; Hidetoshi Koga, all of Sodegaura, Japan

[73] Assignee: Idemitsu Kosan Company Limited, Tokyo, Japan

[21] Appl. No.: 812,755

[22] Filed: Dec. 23, 1991

[30] Foreign Application Priority Data

Dec. 28, 1990 [JP] Japan ............................ 2-408631

[51] Int. Cl.$^5$ ............................................ C07C 277/00
[52] U.S. Cl. .................................................... 564/234
[58] Field of Search ................. 564/234, 353, 354, 402

[56] References Cited

U.S. PATENT DOCUMENTS

| | | | |
|---|---|---|---|
| 3,366,687 | 1/1968 | Ellis et al. | 564/402 |
| 3,960,949 | 6/1976 | Ahrens et al. | 564/234 |
| 4,558,159 | 12/1985 | McCoy et al. | 564/234 |

FOREIGN PATENT DOCUMENTS

| | | | |
|---|---|---|---|
| 0264465 | 11/1988 | Japan . | |
| 0056841 | 2/1969 | Poland | 564/234 |
| 0996706 | 6/1965 | United Kingdom | 564/234 |

*Primary Examiner*—Allen J. Robinson
*Assistant Examiner*—P. O'Sullivan
*Attorney, Agent, or Firm*—Frishauf, Holtz, Goodman & Woodward

[57] ABSTRACT

The present invention relates to a process for the production of a biguanide derivative useful as an intermediate for triazine-type herbicides, in which the biguanide derivative can be produced at high yields by reacting a phenoxyalkylamine salt with dicyandiamide in a solvent containing a paraffinic hydrocarbon having 8 to 15 carbon atoms, or by reacting a free phenoxylakylamine with a hydrogen halide in a solvent containing a paraffinic hydrocarbon having 8 to 15 carbon atoms and reacting the resultant a phenoxyalkylamine salt with dicyandiamide in the same solvent without isolating the phenoxyalkylamine salt.

32 Claims, No Drawings

PROCESS FOR PRODUCING BIGUANIDE DERIVATIVE

BACKGROUND OF THE INVENTION

1. Field of the Invention

The present invention relates to a process for producing a biguanide derivative useful as an intermediate for triazine-type herbicides.

2. Prior Art

As a triazine-type herbicide, JP-A-63-264465 discloses a triazine-type herbicide in which a phenoxyalkylamino group is substituted on a triazine ring, as is shown in the following formula, and this publication describes that the above triazine-type herbicide has remarkable advantages that it has excellent herbicidal effect and exhibits no phytotoxicity on paddy rice.

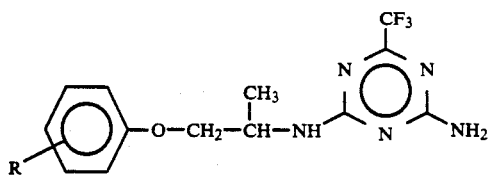

The phenoxyalkylamino-substituted triazine-type herbicide of the above type is obtained, for example, by reacting a biguanide derivative of the formula,

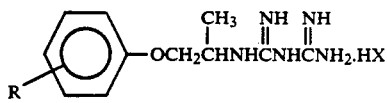

with methyl trifluoroacetate of the formula,

The above biguanide derivative used to obtain the phenoxyalkylamino-substituted triazine-type herbicide is conventionally produced by a method in which a free phenoxyalkylamine is reacted with hydrogen halide to prepare a phenoxyalkylamine salt, and thereafter the phenoxyalkylamine salt is isolated and allowed to react with dicyandiamide. It is suggested in JP-A-63-254465 that an aliphatic hydrocarbon having 7 or less carbon atoms such as n-hexane and n-heptane is used as a solvent for the reaction of a phenoxyalkylamine salt with dicyandiamide.

The defect with the method suggested in the above JP-A-264465 is that the intended biguanide derivative cannot be obtained effectively, especially cannot be obtained under atmospheric pressure, as will be made clear in Comparative Examples to be described later.

Further, as described above, the conventional method of producing a biguanide derivative involves a step of isolating a phenoxyalkylamine salt obtained by a reaction of a free phenoxyalkylamine with hydrogen halide. Therefore, the process is complicated, and the yield of the intended biguanide derivative is inevitably decreased due to the additional complication of the process.

It is therefore a first object of the present invention to provide a process for producing a high-purity biguanide derivative from a phenoxyalkylamine salt at high yields.

It is another object of the present invention to provide a process in which a phenoxyalkylamine salt is prepared from a free phenoxyalkylamine, and thereafter a high-purity biguanide derivative can be produced at high yields in a single operation (one batch) without isolating the obtained phenoxyalkylamine salt.

SUMMARY OF THE INVENTION

In order to attain the above first object, the present inventors have made a study and found that a high-purity biguanide derivative can be obtained at high yields by reacting a phenoxyalkylamine salt with dicyandiamide in a solvent containing a paraffinic hydrocarbon having 8 to 15 carbon atoms.

Further, the present inventors have also found that a high-purity biguanide derivative can be obtained at high yields by reacting a free phenoxyalkylamine with a hydrogen halide in a solvent containing a paraffinic hydrocarbon having 8 to 15 carbon atoms to prepare a phenoxyalkylamine salt, and reacting the resultant phenoxyalkylamine salt with dicyandiamide in the same solvent without isolating the phenoxyalkylamine salt.

The gist of the present invention consists in providing a process for producing a biguanide derivative of the formula [III],

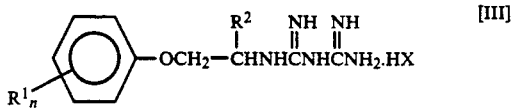

wherein each of $R^1$ and $R^2$ is, independently of other, a $C_1$-$C_4$ alkyl group, n is an integer of 0 to 5, and X is a halogen atom, which comprises reacting a phenoxyalkylamine salt of the formula [I],

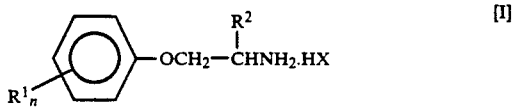

wherein $R^1$, $R^2$, n and X are as defined above, with dicyandiamide of the formula [II],

in a solvent containing a paraffinic hydrocarbon having 8 to 15 carbon atoms (the process is referred to as "present process 1" hereinafter).

The gist of the present invention also consists in providing a process for producing a biguanide derivative of the formula [III],

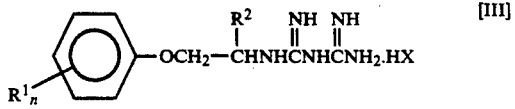

wherein each of $R^1$ and $R^2$ is, independently of other, a $C_1$-$C_4$ alkyl group, n is an integer of 0 to 5, and X is a halogen atom, which comprises reacting a free phenoxyalkylamine of the formula [Ia],

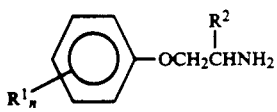

wherein $R^1$, $R^2$ and n are as defined above,
with hydrogen halide in a solvent containing a paraffinic hydrocarbon having 8 to 15 carbon atoms to prepare a phenoxyalkylamine salt of the formula [I],

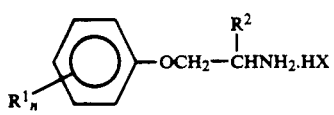

wherein $R^1$, $R^2$, n and X are as defined above,
and reacting the above phenoxyalkylamine salt with dicyandiamide of the formula [II],

in the same solvent without isolating the phenoxyalkylamine salt (the process is referred to as "present process 2" hereinafter).

DETAILED DESCRIPTION OF THE INVENTION

The present invention will be detailed hereinafter.

In the present process 1, the phenoxyalkylamine salt of the formula [I] and the dicyandiamide of the formula [II] are used as a starting material.

In the formula [I] for a phenoxyalkylamine salt as one starting material, each of $R^1$ and $R^2$ is a $C_1$-$C_4$ alkyl group such as methyl, ethyl, linear or branched propyl, or linear or branched butyl. $R^1$ and $R^2$ in the molecule may be the same or different.

In the formula [I], n is an integer of 0 to 5. When n is 0, it means that no $R^1$ is substituted on the phenyl ring. When n is 1 to 5, it means that 1 to 5 $R^1$'s are substituted on the phenyl ring. When n is 2 to 5(2 to 5 $R^1$'s are present), $R^1$'s may be the same or different.

In the formula [I], X is a halogen atom such as chlorine, bromine, fluorine or iodine.

The molar ratio between phenoxyalkylamine salt of the formula [I] and dicyandiamide of the formula [II] (phenoxyalkylamine salt/dicyandiamide) is preferably in the range of 0.5/1 to 1.5/1. In particular, the yield of the biguanide derivative of the formula [III] is remarkably improved when the amount of the dicyandiamide of the formula [II] is equivalent to or an excess of the amount of the phenoxyalkylamine salt of the formula [I] and the above molar ratio is adjusted to 0.85/1 to 1/1.

In the present process 1, the phenoxyalkylamine salt of the formula [I] and the dicyandiamide of the formula [II] are allowed to react in a solvent containing a paraffinic hydrocarbon having 8 to 15 carbon atoms. Due to the use of such a solvent, the intended biguanide derivative having high purity can be obtained at high yields.

In the paraffinic hydrocarbon constituting the solvent, the reasons for limiting the number of its carbon atoms to 8 to 15 are as follows: When the number of carbon atoms is 7 or less, the intended product cannot be obtained effectively, especially cannot be obtained under atmospheric pressure. When the number of carbon atoms is 16 or more, such a hydrocarbon is a solid at an ordinary temperature and poses a problem in its handling.

The hydrocarbon having 8 to 15 carbon atoms is selected from linear paraffins such as n-octane, n-nonane, n-decane, n-undecane, n-dodecane, n-tridecane, n-tetradecane and n-pentadecane; branched paraffins such as 2,2-dimethylhexane, 2,2,4-trimethylhexane, 5-methylnonane and 3-methylundecane; and cycloparaffins such as cyclooctane and n-hexylcyclohexane. That is, the term "paraffinic hydrocarbon" in the present invention is used as a broad concept including branched hydrocarbons and cyclic hydrocarbons in addition to linear hydrocarbons. As a paraffinic hydrocarbon, particularly preferred are those having not less than 10 carbon atoms.

The solvent used in the present invention may be constituted of one or not less than two of the above paraffinic hydrocarbons, or there may be used a paraffinic hydrocarbon mixture such as polymerized butene oil, paraffinic kerosene, or the like. When a paraffinic hydrocarbon mixture such as polymerized butene oil, paraffinic kerosene, or the like is used, a mixture having an average number of carbon atoms in the range of 8 to 15 can be used, and the mixture may contain hydrocarbon(s) having less than 8 or more than 15 carbon atoms. Further, a mixture of the above paraffinic hydrocarbon with an other organic solvent may be used. The organic solvent usable together with the paraffinic hydrocarbon is selected from aromatic hydrocarbons such as o-dichlorobenzene, o-xylene and nitrobenzene; alcohols such as n-octanol, cyclohexanol and benzyl alcohol; and ethers such as ethylene glycol dibutyl ether and triethylene glycol dimethyl ether. When a mixture of the paraffinic hydrocarbon with other organic solvent is used, it is preferred to adjust the content of the paraffinic hydrocarbon in the mixture to not less than 30% by volume, particularly not less than 50% by volume.

The reaction temperature is preferably 120° C. to 200° C., particularly preferably 130° C. to 150° C., although it is not critical. The reaction time is not critical either. However, the reaction time is preferably set for 0.5 to 8 hours, particularly preferably set for 3 to 5 hours. The reaction may be carried out under atmospheric pressure or under elevated pressure.

According to the present process 1 above, there can be obtained a high-purity biguanide derivative from a phenoxyalkylamine salt at high yields, as will be made clear in Examples to be described later.

The present process 2 will be described hereinafter.

In the above-described present process 1, the preliminarily prepared and isolated phenoxyalkylamine salt of the formula [I] is allowed to react with dicyandiamide to obtain the biguanide derivative of the formula [III]. Meanwhile, in the present process 2, a precursor of the phenoxyalkylamine salt of the above formula [I], i.e., a free phenoxyalkylamine of the formula [Ia],

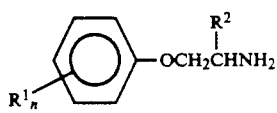

wherein each of $R^1$ and $R^2$ is, independently of other, a $C_1$-$C_4$ alkyl group, and n is an integer of 0 to 5, and hydrogen halide are allowed to react in a solvent containing a paraffinic hydrocarbon having 8 to 15 carbon atoms to prepare the phenoxyalkylamine salt of the above formula [I], and this phenoxyalkylamine salt is allowed to react with the dicyandiamide of the above formula [II] in the same solvent without isolating the phenoxyalkylamine salt, whereby the biguanide derivative of the above formula [III] can be obtained.

In the present process 2, the phenoxyalkylamine of the formula [Ia] and hydrogen halide are used as a starting material.

In the formula [Ia] for phenoxyalkylamine, $R^1$, $R^2$ and n are the same as defined in the formula [I] for the above phenoxyalkylamine salt.

The hydrogen halide used for the reaction with the phenoxyalkylamine is selected from hydrogen chloride, hydrogen bromide, hydrogen fluoride and hydrogen iodide.

The molar ratio of the hydrogen halide (HX) to the phenoxyalkylamine (PAA) of the formula [Ia] (HX/PAA) is preferably 1 to 3. The reason therefor is as follows: When the molar ratio is less than 1, the amount of the hydrogen halide is short of its equivalent amount, and the salt formation is insufficient. When the molar ratio exceeds 3, the hydrogen halide is present in large excess, and unreacted hydrogen halide wastes although the salt formation is sufficient. The molar ratio is particularly preferably 1 to 1.5.

The paraffinic hydrocarbon having 8 to 15 carbon atoms, used as a solvent for the reaction of the phenoxyalkylamine with the hydrogen halide, is specifically selected from those which are used for the reaction of the phenoxyalkylamine salt with dicyandiamide in the above present process 1.

The temperature and time required for the reaction of the phenoxyalkylamine of the formula [Ia] with hydrogen halide are not critical. However, the reaction is preferably carried out at a temperature of 10° C. to 50° C. for 0.5 to 3 hours. This reaction may be carried out at atmospheric pressure or under elevated pressure.

In the present process 2, the phenoxyalkylamine salt obtained above is not isolated, and it is directly allowed to react with dicyandiamide in the same solvent that has been used for the reaction for the formation of the phenoxyalkylamine salt, whereby the intended biguanide derivative is obtained. The phenoxyalkylamine salt and dicyandiamide are allowed to react under the same conditions as those specified concerning the present process 1.

The present process 2 above obviates a step of isolating the phenoxyalkylamine salt, and can hence simplify the process. Further, since the step of forming the phenoxyalkylamine salt and the step of forming the biguanide derivative can be carried out in the same solvent, the amount of the solvent for use can be decreased. Moreover, the present process 2 permits the production of a biguanide derivative having high purity at high yields, which will be made clear in Examples to be described later.

The present process 1 for obtaining a biguanide derivative from the phenoxyalkylamine salt of the formula [I] and the present process 2 for obtaining a biguanide derivative from the free phenoxyalkylamine of the formula [Ia] have been explained above. The free phenoxyalkylamine of the formula [Ia], used as a starting material in the latter process, can be obtained by any one of the following methods (a) to (f). And, the phenoxyalkylamine salt of the formula [I], used in the former process, can be obtained by reacting the phenoxyalkylamine of the formula [I] obtained by any one of the methods (a) to (f) with hydrogen halide.

(a) Reaction between a phenol compound and an aziridine compound.

(b) Amination of 1-alkyl-2-phenoxyethanol with ammonia.

(c) Amination of phenoxyalkyl halide with ammonia.

(d) Amination of phenoxymethyl alkyl ketone with ammonia.

(e) Reduction of phenoxyalkanone oxime.

(f) Amination of 1-alkyl-2-phenoxyethylmethansulfonate with ammonia.

The above methods (a) to (f) will be individually described hereinafter.

Method (a)

In this method, a phenol compound of the formula,

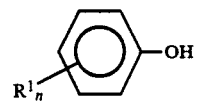

wherein $R^1$ is a $C_1$-$C_4$ alkyl group, and n is an integer of 0 to 5,
and an aziridine compound of the formula,

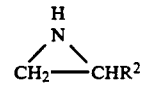

wherein $R^2$ is a $C_1$-$C_4$ alkyl group,
are allowed to react under elevated pressure at a temperature of 100° C. to 250° C., whereby there is obtained a phenoxyalkylamine of the formula [Ia],

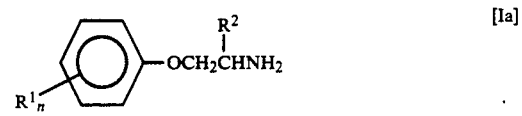

wherein $R^1$, $R^2$ and n are as defined above.

In the above method (a), the phenol compound of the above formula includes phenol per se, o-, m- or p-methylphenol, o-, m- or p-ethylphenol, o-, m- or p- and n-or iso-propylphenol, o-, m- or p- and n-, iso-, sec- or tert-butylphenol, or 2,3-, 2,4-, 2,5-, 2,6-, 3,4-or 3,5-dimethylphenol. The aziridine compound of the above formula refers to propyleneimine, 2-ethylaziridine, 2-n-propylaziridine, 2-iso-propylaziridine, 2-n-butylaziridine, 2-sec-butylaziridine, or 2-tert-butylaziridine. The phenol compound/aziridine compound molar ratio is 0.5 to 10, preferably 3 to 5.

The essential requirement of the above method (a) is that the above phenol compound and aziridine compound are allowed to react under elevated pressure at a temperature of 100° C. to 250° C. Under this requirement, the phenoxyalkylamine can be obtained at high yields.

For the essential requirement of carrying out the reaction under elevated pressure, it is preferred to use a pressure reactor such as an autoclave as a reactor. Depending upon the reaction temperature to be described below, in general, the reaction pressure is preferably kept at a pressure in the range of from more than 1 kg/cm² G to 15 kg/cm² G. The reason therefor is that when the pressure of 1 kg/cm² G is an atmospheric pressure and that when the pressure exceeds 15 kg/cm² G, the formation of by-products increases. The reaction pressure is particularly preferably 5 to 10 kg/cm² G.

It is another essential requirement in the method (a) to set the reaction temperature of 100° C. to 250° C. The reason for this requirement of the reaction temperature of 100° C. to 250° C. is that when the temperature is below 100° C., the reaction hardly proceeds and results in a low yield, and that when the temperature exceeds 250° C., the formation of by-products increases. The reaction temperature is particularly preferably 150° C. to 200° C.

The reaction may be carried out in the absence of a solvent. However, the reaction is preferably carried out in the presence of a solvent, which is selected, for example, from aliphatic hydrocarbon solvents such as hexane, octane and decane; aromatic hydrocarbon solvents such as benzene, toluene and xylene; nitrogen-containing hydrocarbon solvents such as pyridine; chlorinated hydrocarbon solvents such as dichloromethane and chloroform; and polar solvents such as acetonitrile and dimethylformamide. Particularly preferred as a solvent are aliphatic hydrocarbon solvents and aromatic hydrocarbon solvents.

Depending upon the above-described reaction conditions, the reaction time is generally set for 30 minutes to 10 hours, preferably for 1 to 6 hours.

It is known that a phenoxyalkylamine is obtained by reacting a phenol compound with an aziridine compound under an atmospheric pressure at a solvent reflux temperature (J. Am. Chem. Soc. 73 2584 (1951)). The defect with this known method is that the yield of the phenoxyalkylamine is as low as about 50% or less.

Meanwhile, according to the above method (a), a phenol compound and an aziridine compound are allowed to react under elevated pressure at a temperature of 100° C. to 250° C., whereby the phenoxyalkylamine can be obtained at high yields with high selectivity.

Method (b)

In this method, ammonia is allowed to react with 1-alkyl-2-phenoxyethanol of the formula,

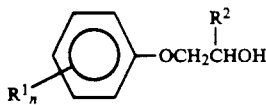

wherein each of R¹ and R² is, independently of other, a C₁-C₄ alkyl group, and n is an integer of 0 to 5, in the presence of a copper-chromium catalyst and hydrogen, whereby there is obtained a phenoxyalkylamine of the formula [Ia],

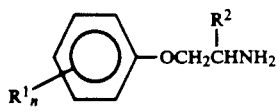

wherein R¹, R² and n are as defined above.

In the above method (b), the 1-alkyl-2-phenoxyethanol used as a starting material includes 1-methyl-2-(3,5-dimethylphenoxy)ethanol, 1-methyl-2-(2,3-dimethylphenoxy)ethanol, 1-methyl-2-(2,5-dimethylphenoxy)ethanol, 1-methyl-2-(2,3,5-trimethylphenoxy)ethanol, 1-methyl-2-(2-methylphenoxy)ethanol, 1-methyl-2-(3-methylphenoxy)ethanol, 1-methyl-2-(4-methylphenoxy)ethanol, 1-methyl-2-(3-ethylphenoxy)ethanol, 1-methyl-2-(3-isopropylphenoxy)ethanol, 1-ethyl-2-(3-methylphenoxy)ethanol, 1-propyl-2-(3-methylphenoxy)ethanol, and 1-methyl-2-phenoxyethanol.

The molar ratio of ammonia (NH₃) to the starting 1-alkyl-2-phenoxyethanol (APE) (NH₃/APE) is preferably 1.0 to 10.0. The reason therefor is that when the molar ratio is less than 1.0, the ammonia amount is short of its stoichiometeric amount, resulting in a low yield of the phenoxyalkylamine, and that when the molar ratio exceeds 10.0, no further improvement in the yield can be expected. The molar ratio is particularly preferably 1.5 to 4.0. That is, when ammonia is reacted with 1-alkyl-2-phenoxyethanol to obtain the phenoxyalkylamine, it is preferred to supply ammonia in the above-specified excess amount relative to 1-alkyl-2-phenoxyethanol.

In the method (b), a copper-chromium catalyst is used in the reaction between 1-alkyl-2-phenoxyethanol and ammonia. Preferred is a copper-chromium catalyst which contains copper and chromium, both as an oxide, in a freely selected mixing ratio and which optionally contains manganese, etc., as an oxide. Particularly preferred is a copper-chromium catalyst which is composed of 40 to 50% of CuO, 40 to 50% of Cr₂O₃ and 0 to 10% of MnO. Specific examples of the copper-chromium catalyst are copper-chromium catalysts N201, N202 and N203 supplied by Nikki Chemical Co. The weight ratio of the copper-chromium catalyst to the organic starting material, 1-alkyl-2-phenoxyethanol, is preferably 0.05 to 1.0. The reason therefor is that when the weight ratio is less than 0.05, neither the yield nor the selectivity is sufficient, and that even when the weight ratio exceeds 1.0, no further improvement in the yield and selectivity can be expected. The catalyst/organic starting material weight ratio is particularly preferably 0.2 to 0.6. The copper-chromium catalyst may be supported on a carrier such as silica, alumina, etc.

In the method (b), the reaction is carried out in the presence of hydrogen, and the hydrogen pressure is preferably set in the range of from 1 to 60 kg/cm²G. The reason therefor is that when the hydrogen pressure is less than 1 kg/cm²G, the yield of the intended product is low, and that when it exceeds 60 kg/cm²G, the yield is not further improved.

The reaction temperature and reaction pressure are not critical. However, the reaction temperature is preferably set from 150° C. to 300° C., particularly preferably from 200° C. to 270° C. Depending upon the reaction temperature, the reaction pressure is preferably set at 10 to 200 kg/cm²G, particularly preferably at 40 to 140 kg/cm². Depending upon the reaction temperature and pressure, the reaction time is preferably set for 1 to 10 hours, particularly preferably for 2 to 8 hours.

According to the disclosure by Polish Patent Laid-open Publication No. 142711, it is known that 1-methyl-2-(2,6-dimethylphenoxy)ethanol included in the 1-alkyl-2-phenoxyethanol is allowed to react with ammonia in the presence of a copper-nickel catalyst and hydrogen, whereby there is obtained 1-(2,6-dimethylphenoxy)-2-propylamine included in the phenoxyalkylamine. The defect with this known method is that a large amount of 2,6-xylenol as a by-product is produced in addition to 1-(2,6-dimethylphenoxy)-2-propylamine and the yield of 1-(2,6-dimethylphenoxy)-2-propylamine is low.

Meanwhile, according to the above method (b), 1-alkyl-2-phenoxyethanol and ammonia are allowed to react in the presence of the copper-chromium catalyst in place of the copper-nickel catalyst used in the above known method, whereby the phenoxyalkylamine can be obtained at high yields with high selectivity.

In addition, the 1-alkyl-2-phenoxyethanol of the formula,

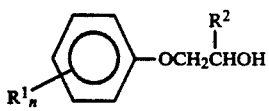

wherein each of $R^1$, $R^2$ and n are as defined above, used as a starting material in the above method (b) can be obtained by reacting a phenol compound of the formula,

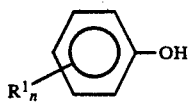

wherein $R^1$ and n are as defined above, with an alkylene oxide of the formula,

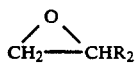

wherein $R^2$ is as defined above,
according to a conventional method.

Method (c)

In this method, ammonia is allowed to react with a phenoxyalkyl halide of the formula,

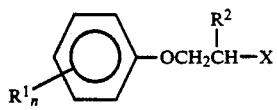

wherein each of $R^1$ and $R^2$ is, independently of other, a $C_1$-$C_4$ alkyl group, X is a halogen atom and n is an integer of 0 to 5,
whereby there is obtained the phenoxyalkylamine of the formula [Ia],

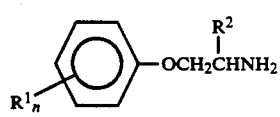

wherein $R^1$, $R^2$ and n are as defined above.

In the above method (c), the phenoxyalkyl halide of the above formula as a starting material includes 1-(3,5-dimethylphenoxy)-2-chloropropane, 1-(2,3-dimethylphenoxy)-2-chloropropane, 1-(2,5-dimethylphenoxy)-2-chloropropane, 1-(2,3,5-trimethylphenoxy)-2-chloropropane, 1-(2-methylphenoxy)-2-chloropropane, 1-(3-methylphenoxy)-2-chloropropane, 1-(4-methylphenoxy)-2-chloropropane, 1-(3-ethylphenoxy)-2-chloropropane, 1-(3-isopropylphenoxy)-2-chloropropane, 1-(3-methylphenoxy)-2-chloropropane, 1-phenoxy-2-chloropropane, 1-(3,5-dimethylphenoxy)-2-bromopropane, and 1-(3-methylphenoxy)-2-bromopropane.

The ammonia which is allowed to react with the above organic starting material is used in the form of a gas, an aqueous solution or an organic solvent solution.

The molar ratio of ammonia ($NH_3$) to the phenoxyalkyl halide (PAX) ($NH_3$/PAX) is preferably 16 to 66. The reason therefor is that when the molar ratio is less than 16, much phenoxyalkyl halide remains and the phenoxyalkylamine is obtained at low yields, and that even when it exceeds 66, no further improvement in the yield can be expected.

The above reaction is preferably carried out in an organic solvent in the presence of a catalyst. The catalyst is selected from alkali metal iodides such as sodium iodide and potassium iodide. The organic solvent is selected from ketones such as acetone and methyl ethyl ketone; ethers such as diethyl ether; cyclic ethers such as tetrahydrofuran and dioxane; alcohols such as methyl alcohol and ethyl alcohol; nitriles such as acetonitrile; chlorinated hydrocarbons such as dichloromethane and chloroform; amides such as N,N-dimethylformamide and N,N-dimethylacetamide; aromatic hydrocarbons such as benzene and toluene; and sulfoxides such as dimethyl sulfoxide.

The reaction temperature, reaction pressure and reaction time are not critical. However, the reaction temperature is preferably 20° C. to 200° C., particularly preferably 50° C. to 150° C. The reaction pressure is preferably atmospheric pressure to 100 kg/cm$^2$G, particularly preferably 7 kg/cm$^2$G to 40 kg/cm$^2$. The reaction time is preferably set for 2 to 10 hours, particularly preferably for 4 to 8 hours.

According to the method (c), ammonia is allowed to react with the phenoxyalkyl halide, whereby the phenoxyalkylamine can be obtained at high yields with high selectivity.

In addition, the phenoxyalkyl halide of the formula,

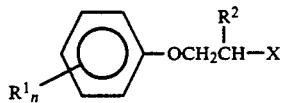

wherein $R^1$, $R^2$, X and n are as defined above, used as a starting material in the method (c) can be obtained by reacting a phenol compound of the formula,

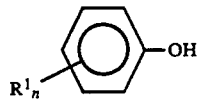

wherein $R^1$ and n are as defined above, with an alkylene oxide of the formula,

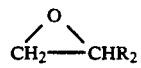

wherein $R^2$ is as defined above,
to prepare 1-alkyl-2-phenoxyethanol of the formula,

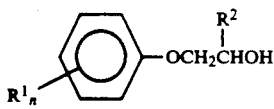

wherein $R^1$, $R^2$ and n are as defined above,
and reacting the 1-alkyl-2-phenoxyethanol with thionyl halide ($SO_2X$), or reacting it with hydrocarbon tetrahalide ($CX_4$) in the presence of triphenylphosphine.

Method (d)

In this method, a phenoxymethyl alkyl ketone of the formula,

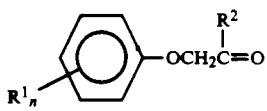

wherein each of $R^1$ and $R^2$ is, independently of other, a $C_1$-$C_4$ alkyl group, and n is an integer of 0 to 5,
is subjected to reductive amination in a hydrous alcohol in the presence of a Raney nickel catalyst, whereby there is obtained the phenoxyalkylamine of the formula [Ia],

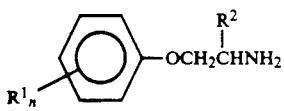

wherein $R^1$, $R^2$ and n are as defined above.

The phenoxymethyl alkyl ketone of the above formula, used as a starting material in the method (c) includes 1-(3,5-dimethylphenoxy)-2-propanone, 1-(2,3-dimethylphenoxy)-2-propanone, 1-(2,5-dimethylphenoxy)-2-propanone, 1-(2,3,5-trimethylphenoxy)-2-propanone, 1-(2-methylphenoxy)-2-propanone, 1-(3-methylphenoxy)-2-propanone, 1-(4-methylphenoxy)-2-propanone, 1-(3-ethylphenoxy)-2-propanone, 1-(3-isopropylphenoxy)-2-propanone, 1-(3-methylphenoxy)-2-butanone, 1-(3-methylphenoxy)-2-pentanone, and 1-phenoxy-2-propanone.

According to the method (d), the above starting material is subjected to reductive amination in a hydrous alcohol in the presence of a Raney nickel catalyst.

The reductive amination can be carried out by supplying the reaction system with hydrogen and an ammonia source. The hydrogen pressure is preferably set at 2 to 80 kg/cm$^2$G. The reason therefor is that when the hydrogen pressure is less than 2 kg/cm$^2$G, the reductive amination does not smoothly proceed, and that when it exceeds 80 kg/cm$^2$G, the formation of by-products increases. The hydrogen pressure is particularly preferably 3 to 50 kg/cm$^2$G. The reaction may be carried out after adjusting the hydrogen pressure to the above-specified range and without supplying hydrogen during the reaction. The reaction may also be carried out while hydrogen is supplied to maintain the hydrogen pressure in the above-specified range.

The ammonia source is introduced into the reaction system in the form of an ammonia gas or ammonia water. The amount of ammonia for use per equivalent of the starting material is 1.0 to 20 equivalents, preferably 1.0 to 15 equivalents.

In the method (d), the reductive amination is carried out in the presence of a Raney nickel catalyst. There are eight types of Raney nickel catalysts, $W_1$, $W_2$, $W_3$, $W_4$, $W_5$, $W_6$, $W_7$ and $W_8$, which differ in activity. In the method (d), all of these Raney nickel catalysts which differ in activity can be used by changing the amount or suitably adjusting other reaction conditions. The amount of the Raney nickel catalyst based on the starting material is 0.5 to 20% by weight, preferably 1.0 to 15.0% by weight.

The method (d) is characterized in that the reductive amination is carried out in a hydrous alcohol. A study by the present inventors has confirmed that the yield of the phenoxyalkylamine is remarkably improved by carrying out the reaction in a hydrous alcohol as compared with the yield attained by carrying out the reaction in an anhydrous alcohol. The alcohol as a component of the hydrous alcohol is selected from lower alcohols such as methanol, ethanol, propanol and butanol. When an ammonia gas is used as the above ammonia source, a mixed solvent prepared by adding water to the above alcohol is used, whereby the reductive amination in a hydrous alcohol can be carried out. When ammonia water is used as the above ammonia source, the above alcohol is used as it is, whereby the reductive amination in a hydrous alcohol can be carried out. Even when ammonia water is used, an alcohol/water mixed solvent can be naturally used. The amount of the hydrous alcohol per 1.0 g of the starting material is preferably 1 to 10 cc. The content of water in the hydrous alcohol is preferably 2 to 70% (v/v), particularly preferably 10 to 60% (v/v).

The reaction temperature is preferably between 30° C. and 180° C., particularly preferably between 40° C. and 150° C. although it is not critical.

The reaction time is generally 30 minutes to 5 hours although it is not particularly critical.

According to the disclosure by JP-A-63-264465, it is known that 1-(3,5-dimethylphenoxy)-2-propane included in the phenoxymethyl alkyl ketone is allowed to react with sodium borocyanide in methanol in the presence of ammonium acetate, whereby there is obtained 1-(3,5-dimethylphenoxy)-2-aminopropane included in the phenoxyalkylamine. The defect with the above known method is that the yield of the 1-(3,5-dimethylphenoxy)-2-aminopropane is as low as about 30%.

Comptes Rendus de l'Academie des Sciences 233 1120 (1951) discloses a method in which 1-phenoxy-2-aminopropane is produced by subjecting 1-phenoxy-2-propane to reductive amination in an alcohol in the presence of a Raney nickel catalyst. According to this literature, however, the reaction is carried out at 100° C. under 100 kg/cm$^2$G, and the yield is as low as about 50%. The alcohol as a reaction solvent is used in such a state that it contains no water. It is therefore necessary to take special care of the alcohol before the reaction.

Meanwhile, for the reductive amination of the phenoxymethyl alkyl ketone, the method (d) employs the reaction conditions (e.g., use of a hydrous alcohol solvent, etc.) which are different from those of the above two known methods, whereby the phenoxyalkylamine can be obtained at high yields with high selectivity.

In addition, the phenoxymethyl alkyl ketone of the formula,

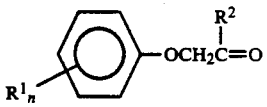

wherein $R^1$, $R^2$ and n are as defined above,
used as a starting material in the above method (d) can be obtained by subjecting a phenol compound of the formula,

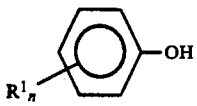

wherein $R^1$ and n are as defined above,
and a halomethyl alkyl ketone of the formula,

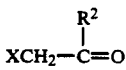

wherein $R^2$ is as defined above and X is a halogen atom, to dehydrohalogenation in a polar aprotic solvent (e.g., DMF, DMSO, 1,3-dimethyl-2-imidazolidinone or sulfolane) in the presence of a base (e.g., sodium carbonate, potassium carbonate or sodium phosphate) and a catalyst (potassium iodide, potassium bromide or sodium iodide).

Method (e)

In this method, 1-phenoxy-2-alkanone oxime of the formula,

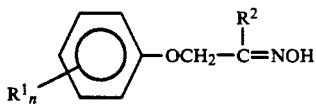

wherein each of $R^1$ and $R^2$ is, independently of other, a $C_1$–$C_4$ alkyl group, and n is an integer of 0 to 5, is reduced with hydrogen, whereby there is obtained a phenoxyalkylamine of the formula [Ia].

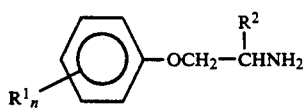

[Ia]

wherein $R^1$, $R^2$ and n are as defined above.

In the method (e), the 1-phenoxyalkanone oxime as a starting material includes 1-(3,5-dimethylphenoxy)-2-propanone oxime, 1-(2,3-dimethylphenoxy)-2-propanone oxime, 1-(2,5-dimethylphenoxy)-2-propanone oxime, 1-(2,3,5-trimethylphenoxy)-2-propanone oxime, 1-(2-methylphenoxy)-2-propanone oxime, 1-(3-methylphenoxy)-2-propanone oxime, 1-(4-methylphenoxy)-2-propanone oxime, 1-(3-ethylphenoxy)-2-propanone oxime, 1-(3-isopropylphenoxy)-2-propanone oxime, 1-(3-methylphenoxy)-2-butanone oxime, 1-(3-methylphenoxy)-2-pentanone oxime, and 1-phenoxy-2-propanone oxime.

In the method (e), the reduction of 1-phenoxy-2-alkanone oxime as a starting material is preferably carried out under a hydrogen pressure of atmospheric pressure to 50 kg/cm$^2$G, particularly atmospheric pressure to 30 kg/cm$^2$G in the presence of a reducing catalyst such as Raney nickel, palladium or platinum. The Raney nickel is suitably selected from Raney nickel catalysts, $W_1$, $W_2$, $W_3$, $W_4$, $W_5$, $W_6$, $W_7$ and $W_8$ as described in the method (d). The amount of the reducing catalyst based on the starting material is preferably 0.5 to 20% by weight, particularly preferably 1 to 15% by weight. The above reaction is preferably carried out in a solvent. The solvent is selected from water, alcohols such as methyl alcohol and ethyl alcohol, ethers such as diethyl ether and dibutyl ether, cyclic ethers such as dioxane and tetrahydrofuran, and organic acids such as acetic acid. The above solvents may be used alone or in combination.

The reaction temperature and time are not critical. However, the reaction temperature is preferably 10° C. to 100° C., particularly preferably 20° C. to 70° C. The reaction time is preferably 0.5 to 10 hours, particularly preferably 1 to 8 hours.

According to the above method (e), the phenoxyalkylamine can be obtained at high yields with high selectivity by reducing 1-phenoxy-2-alkanone oxime with hydrogen.

In addition, the 1-phenoxy-2-alkanone oxime of the formula,

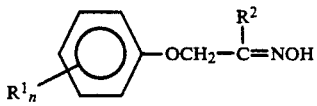

wherein $R^1$, $R^2$ and n are as defined above,
used as a starting material in the method (e) can be obtained by reacting a phenoxymethyl alkyl ketone of the formula,

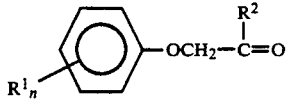

wherein $R^1$, $R^2$ and n are as defined above,
with a hydroxyamine salt in the presence of a base.

In addition, the above phenoxymethyl alkyl ketone can be obtained (i) by reacting a phenol compound of the formula,

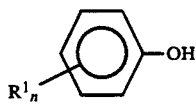

wherein $R^1$ and n are as defined above,
with a halomethyl alkyl ketone of the formula,

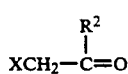

wherein $R^2$ is as defined above and X is a halogen atom, in the presence of a base, or (ii) by dehydrogenating the same 1-alkyl-2-phenoxyethanol of the formula,

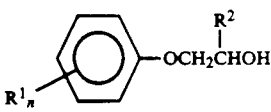

wherein R¹, R² and n are as defined above,
as that used as a starting material in the method (b), in the presence of a copper-chromium catalyst.

Method (f)

In this method, ammonia is allowed to react with 1-alkyl-2-phenoxyethyl-methanesulfonate of the formula,

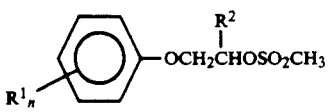

wherein each of R¹ and R² is, independently of other, a $C_1$–$C_4$ alkyl group, and n is an integer of 0 to 5, provided that when n is 2, there is excluded a case where one R¹ is substituted on the 2-position of the benzene ring and the other R¹ is substituted on the 6-position of the benzene ring,
whereby there is obtained a phenoxyalkylamine of the formula [Ia],

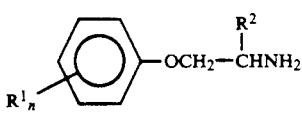

wherein R¹, R² and n are as defined above.

The 1-alkyl-2-phenoxyethyl-methanesulfonate of the above formula, used as a starting material in the method (f), includes 1-methyl-2-(3,5-dimethylphenoxy)ethylmethanesulfonate, 1-methyl-2-(2,3-dimethylphenoxy)ethylmethanesulfonate, 1-methyl-2-(2,5-dimethylphenoxy)ethylmethanesulfonate, 1-methyl-2-(2,3,5-trimethylphenoxy)ethylmethanesulfonate, 1-methyl-2-(2-methylphenoxy)ethylmethanesulfonate, 1-methyl-2-(3-methylphenoxy)ethylmethanesulfonate, 1-methyl-2-(4-methylphenoxy)ethylmethanesulfonate, 1-methyl-2-(3-ethylphenoxy)ethylmethanesulfonate, 1-methyl-2-(3-isopropylphenoxy)ethylmethanesulfonate, 1-ethyl-2-(3-methylphenoxy)ethylmethanesulfonate, 1-propyl-2-(3-methylphenoxy)ethylmethanesulfonate, and 1-methyl-2-phenoxyethylmethanesulfonate.

The amount of ammonia for use per mole of the starting 1-alkyl-2-phenoxyethyl-methanesulfonate is preferably 10 to 30 mols. The ammonia may be supplied in the form of a liquid or a gas, or in the form of an organic solvent or an aqueous solution. The ammonia may be dissolved in an organic solvent/water mixed solvent. The organic solvent is selected from ketones such as acetone and methyl ethyl ketone, ethers such as diethyl ether, cyclic ethers such as tetrahydrofuran and dioxane, alcohols such as methyl alcohol and ethyl alcohol, nitriles such as acetonitrile, halogenated hydrocarbons such as dichloromethane and chloroform, amides such as N,N-dimethylformamide and N,N-dimethylacetamide, aromatic hydrocarbons such as benzene and toluene, and sulfoxides such as dimethylsulfoxide.

In the method (f), even when the organic solvent and/or water are/is used as a solvent, a small amount thereof suffices, or the amount is as small as 0.9 to 4 times the volume of the starting 1-alkyl-2-phenoxyethyl-methanesulfonate.

In the method (f), the presence of a base is not an essential requirement. When used, the base is selected from inorganic or organic bases such as sodium hydroxide, potassium carbonate, potassium bicarbonate, sodium carbonate, sodium bicarbonate, metal sodium, sodium hydride, sodium amide, triethylamine, dimethylaniline and pyridine. The amount of the base for optional use per mole of the starting 1-alkyl-2-phenoxyethyl-methanesulfonate is not more than 1.3 mols.

The reaction temperature, pressure and time are not critical. However, the reaction temperature is 20° C. to 200° C., preferably 50° C. to 130° C., the reaction pressure is from atmospheric pressure to 50 kg/cm²G, preferably from 7 to 40 kg/cm²G, and the reaction time is 2 to 10 hours, preferably 4 to 8 hours.

Finnish Laid-open Patent Publication No. 54292 discloses a method in which ammonia is reacted with 1-methyl-2-(2,6-dimethylphenoxy)ethyl-methanesulfonate in methanol.

In the method disclosed in the above Finnish Laid-open Patent Publication, however, the yield of the intended phenoxyalkylamine is as low as about 65% although ammonia is used in such an amount that is about 38 mols per mole of the starting 1-methyl-2-(2,6-dimethylphenoxy)ethyl-methanesulfonate. Further, the above Finnish Laid-open Patent Publication discloses nothing concerning the reaction of ammonia with 1-alkyl-2-phenoxyethyl-methanesulfonates other than 1-methyl-2-(2,6-dimethylphenoxy)ethyl-methanesulfonate to obtain a corresponding amine.

Meanwhile, according to the above method (f), ammonia is reacted with the starting 1-alkyl-2-phenoxyethyl-methanesulfonate (excluding a case where alkyl groups are substituted on the 2- and 6-positions of the benzene ring) as described above, whereby, even if the amount of ammonia is as small as 10 to 30 times the molar amount of the above starting material, the product, phenoxyalkylamine, can be obtained at high yields with high selectivity as will be made clear in Examples to be described later.

In addition, the 1-alkyl-2-phenoxyethyl-methanesulfonate of the formula,

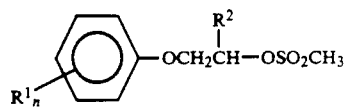

wherein R¹, R² and n are as defined above,
used as a starting material in the method (f) can be obtained by reacting a phenol compound of the formula,

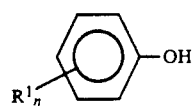

wherein R¹ and n are as defined above,
with an alkylene oxide of the formula,

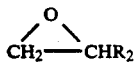

wherein $R^2$ is as defined above,
to prepare 1-alkyl-2-phenoxyethanol of the formula,

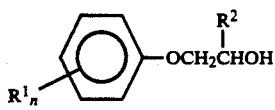

wherein $R^1$, $R^2$ and n are as defined above,
and reacting the 1-alkyl-2-phenoxyethanol with methanesulfonyl chloride in the presence of a base.

The methods (a) to (f) for the production of the phenoxyalkylamine used as a starting material in the present process 2 have been detailed above. The phenoxyalkylamine salt used as a starting material in the present process 1 can be obtained by reacting the phenoxyalkylamine obtained by any one of the above methods (a) to (f) with hydrogen halide.

The present invention will be described hereinafter by reference to Examples. However, the present invention shall not be limited to these Examples.

EXAMPLE 1

Present Process 1

5.0 Grams (23.2 mmol) of 2-(3,5-dimethylphenoxy)isopropylamine hydrochloride and 1.95 g (23.2 mmol) of dicyandiamide were mixed with 50 ml of n-decane, and the mixture was stirred under heat at 130° C. for 4.5 hours. After the reaction, the reaction mixture was cooled to form a precipitate, and the precipitate was recovered by filtration and washed with 10 ml of n-hexane three times. The solvent was removed under reduced pressure to give 6.7 g of an intended product, 2-(3,5-dimethylphenoxy)isopropylbiguanide hydrochloride. This product was quantitatively determined with HPLC (column; Shodex DE-613, developing solvent; 1% phosphoric acid:methanol=5:5 (v/v)). The intended product had a purity of 90%, and its yield was 86%.

Further, the above product was recrystallized from 6.7 ml of water to give 5.5 g of a white crystal. This crystal had a melting point of 185.9° to 187.3° C., and has an IR absorption characteristic at 1,550, 1,600, 1,630, 3,200, 3,300, 3,400 and 3,500 cm$^{-1}$.

EXAMPLES 2-13

Present Process 1

Example 1 was repeated except that the conditions shown in Table 1 were employed, thereby to give excellent results shown in Table 1.

TABLE 1

| Example | Solvent | Amount of solvent (ml) | Amount of dicyandiamide (mmol) | Reaction temperature (°C.) | Reaction time (hr) | Purity (%) | Yield (%) |
|---|---|---|---|---|---|---|---|
| 1 | n-decane | 50 | 23.2 | 130 | 4.5 | 90 | 86 |
| 2 | n-decane | 15 | 23.2 | 130 | 4.5 | 87 | 81 |
| 3 | n-decane | 50 | 23.2 | 130 | 2.0 | 79 | 74 |
| 4 | n-decane | 50 | 23.2 | 140 | 2.0 | 70 | 68 |
| 5 | n-decane/octanol | 50/2.5 | 23.2 | 130 | 4.5 | 83 | 82 |
| 6 | n-nonane | 50 | 23.2 | 130 | 4.5 | 84 | 81 |
| 7 | n-octane/o-dichlorobenzene/n-octanol | 60/20/5 | 23.2 | 130 | 4.5 | 88 | 85 |
| 8 | n-octane/o-dichlorobenzene | 50/50 | 23.3 | 130 | 4.5 | 80 | 75 |
| 9 | Polymerized butene oil *1 | 15 | 23.2 | 130 | 4.5 | 82 | 80 |
| 10 | Paraffinic kerosene *2 | 15 | 23.2 | 130 | 4.5 | 78 | 77 |
| 11 | Polymerized butene oil *1 | 15 | 23.2 | 140 | 4.5 | 89 | 87 |
| 12 | Polymerized butene oil *1 | 35 | 25.5 | 130 | 3.5 | 91 | 91 |
| 13 | Polymerized butene oil *1 | 15 | 25.5 | 130 | 4.5 | 94 | 97 |

Notes:
*1: IP-1620, b.p. 165–196° C., average carbon number 10, supplied by Idemitsu Petrochemical Co., Ltd.
*2: b.p. 180–267° C., average carbon number 12, supplied by Idemitsu Kosan Co., Ltd.

COMPARATIVE EXAMPLE 1

The same experiment as that in Example 1 was carried out under the same conditions as those in Example 1 except that 50 ml of the n-decane was replaced with 100 ml of o-dichlorobenzene. As a result, the intended product had a low purity of 55.7%, and its yield was also as low as 50.1%.

COMPARATIVE EXAMPLE 2

The same experiment as that in Example 1 was repeated under the same conditions as those in Example 1 except that no solvent was used and that the reaction temperature and time were changed to 210° C. and 2.5 hours. No intended product was obtained.

COMPARATIVE EXAMPLE 3

The same experiment as that in Example 1 was repeated under the same conditions as those in Example 1 except that 50 ml of the n-decane was replaced with 100 ml of n-heptane and that the reaction temperature and time were changed to 100° C. and 7 hours. No intended product was obtained.

COMPARATIVE EXAMPLE 4

The same experiment as that in Example 1 was repeated under the same conditions as those in Example 1 except that 50 ml of the n-decane was replaced with 100 mol of n-heptane/o-dichlorobenzene (50 ml/50 ml) and that the reaction temperature and time were changed to 110° C. and 7 hours. No intended product was obtained.

EXAMPLE 14

Present Process 2

4.16 Grams (23. 2 mol) of 2-(3,5-dimethylphenoxy)isopropylamine was dissolved in 21 ml of a polymerized butene oil (IP-1620, b.p. 165° to 196° C., average carbon number 10, supplied Idemitsu Petrochemical Co., Ltd.), and a hydrogen chlorine gas was blown into the mixture to give 2-(3,5-dimethylphenoxy)isopropylamine hydrochloride. Without isolating this hydrochloride, 2.14 g (25.5 mmol) of dicyandiamide was further added, and the resultant mixture was stirred under heat at 130° C. for 3.0 hours. After the reaction, the reaction mixture was cooled to form a precipitate, and the precipitate was washed with 10 ml of n-hexane three times. The solvent was removed under reduced pressure to give 6.87 g of an intended product, 2-(3,5-dimethylphenoxy)isopropylbiguanide hydrochloride. This product was quantitatively determined with HPLC (column; Shodex DE-613, developing solvent; 1% phosphoric acid:methanol=5:5 (v/v)). The intended product had a purity of 85%, and its yield was 84%.

Further, the above product was recrystallized from 6.9 ml of water to give 5.5 g of a white crystal. This crystal had a melting point of 185.9° to 187.3° C., and had an IR absorption characteristic at 1,550, 1,600, 1,630, 3,200, 3,300, 3,400 and 3,500 cm$^{-1}$.

EXAMPLES 15 AND 16

Present Process 2

Example 14 was repeated except that the conditions shown in Table 2 were employed, thereby to give excellent results shown in Table 2.

EXAMPLE 17

Method (a)

24.4 Grams (0.20 mol) of 3,5-dimethylphenol and 3.8 g (0.067 mmol) of propyleneimine in 20 ml of toluene were allowed to react in an autoclave at 10 kg/cm$^2$G at 200° C. for 1 hour. The reaction product was dispersed in 50 ml of ether, and then subjected to extraction with 50 ml of 5% hydrochloric acid three times. The water layer of the product was neutralized with sodium hydroxide, and the product was subjected to extraction with 50 ml of ether three times. The ether layer was washed and dried. Then, ether was distilled off, and the residue was distilled under reduced pressure to give 8.3 g of 1-(3,5-dimethylphenoxy)-2-propylamine as a component having a boiling point of 87° to 89° C./0.3 mmHg. Its yield was as high as 70%.

$^1$H-NMR: ($\delta$) 1.14 (d, 3H), 1.45 (s, 2H), 2.27 (s, 6H), 3.1–3.9 (m, 3H), 6.4–6.7 (m, 3H)

IR: (cm$^{-1}$) 3,380, 3,300, 3,020, 1,615, 1,598, 1,460, 1,380, 1,165, 1,150

COMPARATIVE EXAMPLE 5

The reaction according to the method described in a known literature [J. Am. Chem. Soc., 73 2584 (1951)] was carried out by the use of the same starting materials as those used in Example 17. That is, 24.4 g (0.20 mol) of 3,5-dimethylphenol was dissolved in 100 ml of chloroform, and the resultant mixture was refluxed under atmospheric pressure. A solution prepared by dissolving 3.8 g (0.067 mol) of propyleneimine in 20 ml of chloroform was added dropwise over 30 minutes, and the refluxing was further continued for 3 hours. The reaction product was subjected to extraction with 50 ml of 5% hydrochloric acid three times, and then the water layer of the product was neutralized with sodium hydroxide. The water layer was subjected to extraction with 50 ml of ether three times. The ether layer was washed with water and dried. Then, ether was distilled off, and the residue was distilled under reduced pressure to give 3.9 g of 1-(3,5-dimethylphenoxy)-2-propylamine. Its yield was as low as 33%.

EXAMPLE 18

Method (a)

21.6 Grams (0.20 mol) of m-cresol and 2.3 g (0.04 mol) of propyleneimine in 20 ml of n-decane were allowed to react in an autoclave at 5 kg/cm$^2$G at 150° C. for 6 hours. Thereafter, the resultant reaction product was treated in the same manner as in Example 17 to give 3.8 g of 1-(3-methylphenoxy)-2-propylamine. Its yield was as high as 57%.

TABLE 2

| Example | Solvent | Amount of solvent (ml) | Amount of dicyandiamide (mmol) | Reaction temperature (°C.) | Reaction time (hr) | Purity (%) | Yield (%) |
|---|---|---|---|---|---|---|---|
| 14 | Polymerized butene oil *1 | 21 | 25.5 | 130 | 3 | 85 | 84 |
| 15 | Polymerized butene oil *1 | 21 | 25.5 | 130 | 4.5 | 79 | 76 |
| 16 | Polymerized butene oil *1 | 21 | 25.5 | 140 | 3.0 | 81 | 78 |

Notes:
*1: IP-1620, b.p. 165–169° C., average carbon number 10, supplied by Idemitsu Petrochemical Co., Ltd.

$^1$H-NMR: (δ) 1.15 (d, 3H), 1.68 (s, 2H), 2.30 (s, 3H), 3.1–3.9 (m, 3H), 6.6–7.3 (m, 4H)

IR: (cm$^{-1}$) 3,390, 3,310, 3,050, 1,610, 1,593, 1,468, 1,387, 1,050

EXAMPLE 19

Method (b)

A 150 cc autoclave was charged with 50.0 g (277 mmol) of 1-methyl-2-(3,5-dimethylphenoxy)ethanol, 15.4 g of a copper-chromium catalyst (N202, supplied by Nikki Chemical Co.: CuO 44–46%, Cr$_2$O$_3$ 43–44%, MnO$_2$ 4–5%) preliminarily activated under a hydrogen current at 200° to 300° C. for 3 hours and 7.5 g (440 mmol) of ammonia, and the resultant mixture was stirred under a hydrogen pressure of 40 kg/cm$^2$G at 250° C. for 2 hours. After the reaction mixture was allowed to cool, the pressure of excess ammonia and hydrogen was released, and the catalyst was removed by filtration. And, 200 ml of ethyl ether was added to the filtrate, and the mixture was subjected to extraction with 200 ml of a 20% hydrochloric acid aqueous solution. The extracted water layer was rendered alkaline with a 20% sodium hydroxide aqueous solution, and it was subjected to extraction with 200 ml of ethyl ether. The organic layer was dried over anhydrous sodium sulfate, and then the solvent was distilled off under reduced pressure to give 21.4 g of 1-(3,5-dimethylphenoxy)-2-aminopropane (yield 43%). This yield is higher than that which could be attained by the conventional method described in JP-A-63-264465. The starting 1-methyl-2-(3,5-dimethylphenoxy)ethanol in an amount of 23.9 g (48%) was recovered from the organic layer extracted with the hydrochloric acid aqueous solution. The selectivity of the intended product, calculated on the basis of the amount obtained by deducting an unreacted starting material from the total amount of the starting material, was 82%. This selectivity was also higher than that which could be attained by the conventional method described in Polish Laid-open Patent Publication No. 142,711.

EXAMPLES 20-25

Method (b)

Example 19 was repeated except that the reaction conditions were changed as shown in Table 3. Table 3 shows the yields and selectivities of the products obtained. As is clearly shown in Table 3, 1-(3,5-dimethylphenoxy)-2-aminopropane was obtained at high yields with high selectivity.

(i) 3.3 Milliliter (45 mmol) of thionyl chloride was added dropwise to a solution prepared by dissolving 7.38 g (41 mmol) of 1-methyl-2-(3,5-dimethylphenoxy)ethanol in 20 ml of toluene, and the resultant mixture was refluxed in an oil bath at 100° to 110° C. for 4 hours. The reaction solution was cooled, and then washed consecutively with 50 ml of a saturated sodium hydrogencarbonate aqueous solution and 50 ml of a saturated common salt water. The resultant organic layer was dried over 10 g of anhydrous sodium sulfate, and toluene was removed under reduced pressure to give 7.56 g of oily 1-(3,5-dimethylphenoxy)-2-chloropropane (yield 92.9%).

(ii) 0.94 Gram (3.6 mmol) of triphenylphosphine and 1.49 g (4.5 mmol) of carbon tetrabromide were added to a solution prepared by dissolving 0.54 g (3 mmol) of 1-methyl-2-(3,5-dimethylphenoxy)ethanol in 10 ml of methylene chloride, and the resultant mixture was stirred at room temperature for 30 minutes. After the reaction, the solid was separated by filtration, and the remaining methylene chloride solution was concentrated under reduced pressure. The residue was purified by silica gel column chromatography (hexane/ethyl acetate=5:1 (v/v)) to give 0.54 g of 1-(3,5-dimethylphenoxy)-2-bromopropane (yield 74.7%).

(2) 1-(3,5-Dimethylphenoxy)-2-aminopropane was produced as follows.

A 100 ml autoclave was charged with 1.96 g (9.8 mmol) of 1-(3,5-dimethylphenoxy)-2-chloropropane, 10 ml of ethanol and 0.2 g of sodium iodide, and then 40 ml of a 28% ammonia aqueous solution was added. The mixture was continuously stirred at 130° C. for 8 hours to complete the reaction. After allowed to cool, the reaction mixture was transferred into a 500 ml beaker with 50 ml of water and 20 ml of diethyl ether. A 20% hydrochloric acid aqueous solution was added to the reaction mixture until it became acidic, and the mixture was washed with 20 ml of diethyl ether three times. While the water layer was cooled, a 20% sodium hydroxide aqueous solution was added to make it alkaline, and the water layer was subjected to extraction with 50 ml of diethyl ether three times, and dried over 10 g of anhydrous sodium sulfate. Then, the solvent was distilled off under reduced pressure to give 1.48 g of 1-(3,5-dimethylphenoxy)-2-aminopropane (yield 83.7%).

EXAMPLE 27

Method (c)

A 20 ml autoclave was charged with 4.20 g (17.3

TABLE 3

| Example | Starting Material (g) | Copper-chromium catalyst (g) | Ammonia (g) | Hydrogen pressure (kg/cm$^2$G) | Reaction temperature (°C.) | Reaction time (hr) | Product Yield (%) | Selectivity (%) |
|---|---|---|---|---|---|---|---|---|
| 19 | 50.0 | 15.4 | 7.5 | 40 | 250 | 2 | 43 | 82 |
| 20 | 50.0 | 15.4 | 14.2 | 40 | 250 | 4 | 52 | 80 |
| 21 | 50.0 | 15.4 | 10.9 | 40 | 250 | 4 | 49 | 77 |
| 22 | 50.0 | 15.4 | 10.9 | 40 | 230 | 4 | 48 | 80 |
| 23 | 50.0 | 15.4 | 7.5 | 25 | 230 | 5 | 43 | 80 |
| 24 | 30.0 | 15.4 | 8.5 | 25 | 230 | 5 | 60 | 78 |
| 25 | 30.0 | 15.4 | 11.3 | 15 | 240 | 7 | 66 | 84 |

EXAMPLE 26

Method (c)

(1) 1-(3,5-Dimethylphenoxy)-2-bromopropane as a starting material was prepared as follows.

mmol) of 1-(3,5-dimethylphenoxy)-2-bromopropane, 4 ml of methanol and 0.03 g of sodium iodide, and the autoclave was cooled in a dry ice.acetone bath. The pressure in the autoclave was reduced, and 7 g of liquid ammonia was added. The autoclave was allowed to stand until its temperature reached room temperature, and the mixture was continuously stirred at 130° C. for 7 hours to finish the reaction. After allowed to cool, the reaction mixture was post-treated in the same manner as in Example 26 to give 1.66 g of 1-(3,5-dimethylphenoxy)-2-aminopropane (yield 53.8%).

EXAMPLES 28-33

Method (c)

Example 26 was repeated except that the reaction conditions were changed as shown in Table 4. Table 4 shows yields of the products. As is clear in Table 4, 1-(3,5-dimethylphenoxy)-2-aminopropane was obtained at high yields.

TABLE 4

| Example | 28% ammonia water (ml) | Solvent ethanol (ml) | Catalyst (NaI) (g) | Yield (%) |
|---|---|---|---|---|
| 26 | 40 | 10 | 0 | 83.7 |
| 28 | 10 | 5 | 0.2 | 55.1 |
| 29 | 15 | 5 | 0.2 | 53.5 |
| 30 | 20 | 10 | 0.2 | 70.9 |
| 31 | 30 | 10 | 0.2 | 79.6 |
| 32 | 32 | 10 | 0.2 | 78.0 |
| 33 | 40 | 10 | 0 | 72.4 |
| 27 | liq. NH3; 7 g | methanol 4 ml | 0.03 | 53.8 |

Note: In Example 27, 1-(3,5-dimethylphenoxy)-2-bromopropane was used as a starting material, while in the other Examples, 1-(3,5-dimethylphenoxy)-2-chloropropane was used.

EXAMPLE 34

Method (d)

(1) 1-(3,5-Dimethylphenoxy)-2-propanone as a starting material was prepared as follows.

A 500 ml three-necked flask was charged with 10.0 g (82.0 mmol) of 3,5-xylenol, 14.6 g (107 mmol) of anhydrous potassium carbonate, 1.0 g (6.7 mmol) of sodium iodide and 20 ml of DMF, and the mixture was heated up to 80° C. Then, while the mixture was stirred, a mixture of 10.0 g (107 mmol) of chloroacetone with 10 ml of DMF was added over 1 hour. After the addition, the resultant mixture was stirred at 80° C. for 30 minutes, and the reaction mixture was cooled. The reaction mixture was filtered, and the solid was washed with DMF. The filtrate and the washing liquid, DMF, were mixed together, and DMF was distilled off under reduced pressure. The residue was distilled under reduced pressure to give 13.3 g of a fraction having a boiling point of 88° C. under a reduced pressure of 0.35 mmHg. This fraction was found to be 1-(3,5-dimethylphenoxy)-2-propanone, and the yield thereof was 91.2%.

(2) 1-(3,5-Dimethylphenoxy)-2-aminopropane was produced as follows.

A 150 ml autoclave was charged with 20.0 g (112 mmol) of 1-(3,5-dimethylphenoxy)-2-propane, 0.5 g of a Raney nickel catalyst (W-7), 25 ml of methanol and 5 ml of water as a solvent, and while the mixture was cooled, 4.78 g (281 mmol) of ammonia was added. The ammonia was supplied in the form of a gas. The mixture was stirred under a hydrogen pressure of 40 kg/cm$^2$G at 80° C. for 3 hours. The pressure of excess ammonia and hydrogen was released. Thereafter, the catalyst was separated by filtration, and the filtrate was concentrated under reduced pressure. The residue was dissolved in 100 ml of ethyl ether, and the mixture was subjected to extraction with a 20% hydrochloric acid aqueous solution. The extracted water layer was made alkaline with a 20% sodium hydroxide aqueous solution, and then subjected to extraction with 100 ml of ethyl ether. The extracted organic layer was distilled under reduced pressure to give 16.3 g of 1-(3,5-dimethylphenoxy)-2-aminopropane (yield 81%). This product had a boiling point of 113° C./3 mmHg.

EXAMPLES 35-48

Method (d)

1-(3,5-Dimethylphenoxy)-2-propanone was subjected to reductive amination under conditions shown in Tables 5 and 6 to give 1-(3,5-dimethylphenoxy)-2-aminopropane. Tables 5 and 6 show the yields of products obtained. Table 5 also shows the conditions and result in the above Example 34. As is clear in Tables 5 and 6, 1-(3,5-dimethylphenoxy)-2-aminopropane was obtained at high yields.

TABLE 5

| Example | Starting material | Temperature (°C.) | Time (hr) | Raney nickel | Ammonia | Hydrogen pressure (atm) | Solvent | Yield (%) |
|---|---|---|---|---|---|---|---|---|
| 34 | 20 g (112 mM) | 80 | 3 | W-7 0.5 g | NH3 gas 4.78 g (281 mM) | 40 | MeOH 25 ml water 5 ml | 81 |
| 35 | 10 g (56 mM) | 80 | 3 | W-2 0.25 g | NH3 gas 3.65 g (215 mM) | 40 | MeOH 11.25 ml water 3.75 ml | 77 |
| 36 | 10 g (58 mM) | 80 | 3 | W-2 0.25 g | NH3 gas 2.36 g (139 mM) | 40 | MeOH 11.25 ml water 3.75 ml | 80 |
| 37 | 1.0 g (5.6 mM) | 80 | 2 | W-7 0.08 g | 28% NH3 water 3 ml (49 mM) | 3 | MeOH 6 ml | 70 |
| 38 | 1.0 g (5.6 mM) | 80 | 2 | W-7 0.05 g | 28% NH3 water 3 ml (49 mM) | 6 | MeOH 6 ml | 75 |
| 39 | 1.0 g (5.6 mM) | 50 | 3 | W-7 0.05 g | 28% NH3 water 3 ml (49 mM) | 6 | MeOH 6 ml | 73 |
| 40 | 20 g (112 mM) | 80 | 3 | W-7 0.5 g | NH3 gas 4.78 g (281 mM) | 18* | MeOH 25 ml water 5 ml | 82 |
| 41 | 10 g (56 mM) | 80 | 3 | W-2 0.5 g | NH3 gas 2.4 g | 40 | MeOH 12.5 ml water 2.5 ml | 77 |

TABLE 5-continued

| Example | Starting material | Temperature (°C.) | Time (hr) | Raney nickel | Ammonia | Hydrogen pressure (atm) | Solvent | Yield (%) |
|---|---|---|---|---|---|---|---|---|
| | | | | | (140 mM) | | | |

*Hydrogen was continuously added.

TABLE 6

| Example | Starting material | Temperature (°C.) | Time (hr) | Raney nickel | Ammonia | Hydrogen pressure (atm) | Solvent | Yield (%) |
|---|---|---|---|---|---|---|---|---|
| 42 | 10 g (56 mM) | 80 | 3 | W-2 0.05 g | 28% NH₃ water 8.5 ml | 40 | MeOH 16.6 ml water 8.3 ml | 79 |
| 43 | 10 g (56 mM) | 80 | 3 | W-2 0.05 g | 28% NH₃ water 6.8 ml | 30 | MeOH 12.6 ml water 6.3 ml | 83 |
| 44 | 10 g (56 mM) | 80 | 3 | W-2 0.05 g | 28% NH₃ water 3.7 ml | 20 | MeOH 7.4 ml water 3.7 ml | 82 |
| 45 | 10 g (56 mM) | 80 | 3 | W-2 0.05 g | 28% NH₃ water 5.1 ml | 20 | MeOH 10 ml water 5 ml | 85 |
| 46 | 10 g (56 mM) | 90 | 3 | W-2 0.025 g | 28% NH₃ water 5.1 ml | 20 | MeOH 10 ml water 5 ml | 81 |
| 47 | 10 g (56 mM) | 100 | 3 | W-2 0.025 g | 28% NH₃ water 5.1 ml | 20 | MeOH 6.8 ml water 3.4 ml | 81 |
| 48 | 10 g (56 mM) | 120 | 3 | W-2 0.025 g | 28% NH₃ water 5.1 ml | 20 | MeOH 6.8 ml water 3.4 ml | 85 |

EXAMPLE 49

Method (e)

(1) 1-(3,5-Dimethylphenoxy)-2-propanone oxime as a starting material was prepared as follows.

(i) 5.0 Grams (28 mmol) of 1-methyl-2-(3,5-dimethylphenoxy)ethanol was dissolved in 10 ml of tetralin, and 0.5 g of a copper-chromium catalyst (203 SD, supplied by Nikki Chemical Co., Ltd.) was added. The resultant mixture was stirred under a nitrogen current (0.1 liter/minute) at 210° C. for 8 hours. The catalyst was removed by filtration, and the filtrate was distilled under reduced pressure to give 3.41 g of 1-(3,5-dimethylphenoxy)-2-propanone (boiling point: 88° C./0.35 mmHg, yield 69%).

Further, the above procedure was repeated under the conditions shown in the following Table 7 to give favorable results.

TABLE 7

| Catalyst | Solvent | Temperature (°C.) | Time (hr) | Yield (%) |
|---|---|---|---|---|
| 203 | dodecane 50 ml | 190 | 8 | 67 |
| 203 | tetralin 5 ml | 190 | 8 | 63 |
| 203 | KSK-280 5 ml | 240 | 1 | 65 |
| 203SD | KSK-280 5 ml | 240 | 2 | 64 |
| 211B | KSK-280 5 ml | 250 | 2 | 69 |

Catalyst: copper-chromium catalyst supplied by Nikki Chemical Co., Ltd.
KSK-280: Synthetic alkylnaphthalene type solvent supplied by Kureha Chemical Co., Ltd.

(ii) 10.0 Grams (56 mmol) of 1-(3,5-dimethylphenoxy)-2-propanone was dissolved in 50 ml of ethanol, and 5.53 g (34 mmol) of hydroxylamine sulfate and 5.66 g (67 mmol) of sodium hydrogencarbonate were added. And, the resultant mixture was stirred at room temperature for 4 hours, and 50 ml of water was added. Ethanol was distilled off under reduced pressure, and the resultant solid precipitate was recovered by filtration, washed with water and dried to give 10.2 g of 1-(3,5-dimethylphenoxy)-2-propanone oxime (yield 92%).

The above procedure was repeated under the conditions shown in the following Table 8 to give favorable results.

TABLE 8

| Hydroxylamine salt | Base | Solvent | | Yield (%) |
|---|---|---|---|---|
| hydroxylamine sulfate 5.53 g (34 mmol) | sodium carbonate 7.14 g (67 mmol) | ethanol water | 50 mmol 50 mmol | 91 |
| hydroxylamine hydrochloride 4.68 g (67 mmol) | sodium hydrogencarbonate 5.66 g (67 mmol) | methanol | 50 ml | 75 |

(2) 1-(3,5-Dimethylphenoxy)-2-aminopropane was produced as follows.

10.0 Grams (52 mmol) of 1-(3,5-dimethylphenoxy)-2-propanone oxime was dissolved in 50 ml of ethanol in an autoclave, and 1.0 g of a Raney nickel catalyst (W-2) was added. The resultant mixture was stirred under a hydrogen pressure of 5 kg/cm²G at 50° to 60° C. for 1 hour. The catalyst was separated by filtration, and the filtrate was concentrated under reduced pressure. The residue was dissolved in 50 ml of ethyl ether, and the mixture was subjected to extraction with a 20% hydrochloric acid aqueous solution. The extracted water layer was made alkaline with a 20% sodium hydroxide aqueous solution, and subjected to extraction with 50 ml of ethyl ether. The extracted organic layer was distilled under reduced pressure to give 8.01 g (yield 86%) of 1-(3,5-dimethylphenoxy)2-aminopropane (boiling point 113° C./3 mmHg).

EXAMPLES 50-52

Method (e)

Example 49 was repeated except that the conditions were changed as shown in Table 9. Table 9 shows the yields of products obtained. As is clear in Table 9, 1-(3,5-dimethylphenoxy)-2-aminopropane was obtained at high yields.

TABLE 9

| Example | Catalyst | Solvent | Hydrogen pressure | Temperature (°C.) | Time (hr) | Yield (%) |
| --- | --- | --- | --- | --- | --- | --- |
| 49 | Raney nickel 1.0 g | ethanol 50 ml | 5 kg/cm$^2$ | 50–60 | 1 | 86 |
| 50 | Raney nickel 0.5 g | ethanol 50 ml | 5 kg/cm$^2$ | 50 | 6 | 77 |
| 51 | Raney nickel 1.0 g | methanol 50 ml | 5 kg/cm$^2$ | 50 | 4.5 | 71 |
| 52 | 5% palladium carbon 5.0 g | ethanol 50 ml | atmospheric pressure | 20 | 7 | 71 |

EXAMPLE 53

Method (f)

(1) 1-Methyl-2-(3,5-dimethylphenoxy)ethyl-methanesulfonate as a starting material was prepared as follows.

(i) Synthesis of 1-methyl-2-(3,5-dimethylphenoxy)ethanol

A 500 ml three-necked flask was charged with 51.88 g (425 mmol) of 3,5-xylenol, 29.6 g (510 mmol) of propylene oxide and 4.25 g (42 mmol) of triethylamine, and the resultant mixture was refluxed under heat at 90° C. for 1 hour and at 110° C. for 4 hours. The reaction product was recrystallized from hexane to give 1-methyl-2-(3,5-dimethylphenoxy)ethanol.

Recovery 67.76 g (yield 88.5%)

Melting point 48.7°–49.5° C.

| Elemental analysis | C | H | O |
| --- | --- | --- | --- |
| Found (%) | 73.22 | 9.14 | 17.87 |
| Calculated (%) | 73.3 | 8.94 | 17.75 |

(ii) Synthesis of 1-methyl-2-(3,5-dimethylphenoxy)ethyl-methanesulfonate 9.82 Grams (54 mmol) of the 1-methyl-(3,5-dimethylphenoxy)ethanol and 12.93 g (162 mmol) of pyridine were dissolved in 20 ml of chloroform, and while the resultant solution was cooled in an ice salt bath, 6.86 g (59 mmol) of methanesulfonyl chloride was dropwise added to the solution. After the addition, the resultant mixture was stirred at room temperature for 8 hours. The reaction mixture was consecutively washed with 30 ml of water, 30 ml of a saturated sodium hydrogencarbonate aqueous solution, 30 ml of a 5% hydrochloric acid aqueous solution and a saturated common salt water, and then dried over anhydrous sodium sulfate. The solvent was distilled off under reduced pressure, and the residue was recrystallized from hexane/ethyl acetate to give 1-methyl-2-(3,5-dimethylphenoxy)ethyl-methanesulfonate.

Recovery 11.91 g (yield 84.6%)

Melting point 73.5°–75.0° C.

| Elemental analysis | C | H | S | O |
| --- | --- | --- | --- | --- |
| Found (%) | 56.05 | 6.83 | 12.10 | 25.29 |
| Calculated (%) | 55.79 | 7.02 | 12.41 | 24.77 |

(2) 1-(3,5-Diemthylphenoxy)-2-aminopropane was produced as follows.

A 20 cc autoclave was charged with 5.42 g (21 mmol) of 1-methyl-2-(3,5-dimethylphenoxy)ethyl-methanesulfonate and 6 ml of methanol, and ammonia was added in an amount of 7.67 g which was 20 times, by mole, as much as the above methanesulfonate. The mixture was continuously stirred at 100° C. for 8 hours to finish the reaction. After the reaction mixture was allowed to cool, remaining ammonia was removed, and the reaction mixture was transferred into a 500 ml beaker with 50 ml of water and 20 ml of ethyl ether. A 20% hydrochloric acid aqueous solution was added until the reaction liquid was made acidic, and the reaction liquid was washed with 50 ml of diethyl ether three times. Then, while the water layer was cooled, a 20% sodium hydroxide aqueous solution was added to make it alkaline, and the reaction liquid was subjected to extraction with 50 ml of diethyl ether three times. The extract was dried over 10 g of anhydrous sodium sulfate, and the solvent was removed under reduced pressure to give 3.25 g of 1-(3,5-dimethylphenoxy)-2-aminopropane (boiling point 113° C./3 mmHg). This amount of 3.25 g corresponded to a yield of 86.6%, or was very high. The results of NMR and IR analyses were as follows.

$^1$H-NMR: (δ) 1.14 (d, 3H), 1.45 (s, 2H), 2.27 (s, 6H), 3.1–3.9 (m, 3H), 6.4–6.7 (m, 3H)

IR: (cm$^{-1}$) 3,380, 3,300, 3,020, 1,615, 1,598, 1,460, 1,380, 1,165, 1,150

EXAMPLES 54–59

Method (f)

Example 53 was repeated except that the molar ratio of ammonia to the methanesulfonate, the amount and kind of the solvent, the reaction temperature and the reaction time were changed. Table 10 shows the results together with the result in Example 53. As is clear in Table 10, even with small amount of ammonia, 1-(3,5-dimethylphenoxy)-2-aminopropane was obtained at high yields.

TABLE 10

| | Reaction Conditions | | | | |
| --- | --- | --- | --- | --- | --- |
| Example | Molar ratio of NH$_3$ | Solvent (ml) | Temperature (°C.) | Time (hr) | Yield (%) |
| 53 | 20 | MeOH, 6 | 100 | 8 | 86.6 |
| 54 | 16 | H$_2$O, 2.8 EtOH, 5 | 130 | 8 | 66.8 |
| 55 | 21 | MeOH, 6 | 80 | 6.5 | 84.7 |
| 56 | 15 | MeOH, 6 | 100 | 4 | 79.4 |
| 57 | 20 | MeOH, 6 | 100 | 4 | 96.1 |
| 58 | 19.8 | MeOH, 6 | 120 | 2 | 82.2 |
| 59 | 19.2 | — | 100 | 4 | 63.2 |

As demonstrated by the above Examples, the present invention has achieved the production of a high-purity biguanide derivative at high yields by reacting a phenoxyalkylamine salt with dicyandiamide in a solvent containing a paraffinic hydrocarbon having 8 to 15 carbon atoms.

Further, the present invention has achieved the production of a high-purity biguanide derivative at high yields by reacting a free phenoxyalkylamine with hydrogen halide in a solvent containing a paraffinic hydrocarbon having 8 to 15 carbon atoms to prepare a phenoxyalkylamine salt, and reacting the resultant phenoxyalkylamine salt with dicyandiamide in the same solvent used above without isolating the phenoxyalkylamine salt.

Furthermore, the present invention has achieved the production, at high yields, of a phenoxyalkylamine and a salt thereof used as a starting material in the production of the above biguanide derivative.

What is claimed is:

1. A process for producing a biguanide compound of the formula (III),

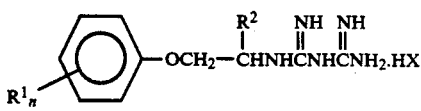
(III)

wherein each of $R^1$ and $R^2$ is, independently, a $C_1$–$C_4$ alkyl group, n is an integer of 0 to 5, and X is a halogen atom, which comprises reacting a phenoxyalkylamine salt of the formula (I),

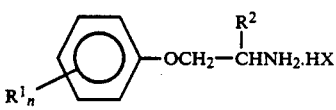
(I)

wherein $R^1$, $R^2$, n and X are as defined above, with dicyandiamide of the formula (II),

(II)

in a solvent containing a paraffinic hydrocarbon having 8 to 15 carbon atoms,
said phenoxyalkylamine salt of the formula (I) and said dicyandiamide of the formula (II) being in a phenoxyalkylamine salt/dicyandiamide molar ratio of 0.5/1 to 1.5/1 and the process being carried at a temperature of 120° C. to 200° C.

2. The process according to claim 1, wherein the reaction is carried out under atmospheric pressure.

3. The process according to claim 1, wherein the reaction is carried out under elevated pressure.

4. The process according to claim 1, wherein the paraffinic hydrocarbon having 8 to 15 carbon atoms is selected from the group consisting of n-octane, n-nonane, n-decane, n-undecane, n-dodecane, n-tridecane, n-tetradecane, n-pentadecane, 2,2-dimethylhexane, 2,2,4-trimethylexane, 5-methylnonane, 3-methylundecane, cycloctane and n-hexylcyclohexane.

5. The process according to claim 4, wherein the temperature is 130° C. to 150° C. and the process being carried out for a period of time of 0.5 to 8 hours.

6. The process according to claim 1, wherein the phenoxyalkylamine salt/dicyandiamide molar ratio is 0.85/1 to 1/1.

7. The process according to claim 1, wherein the solvent containing a paraffinic hydrocarbon is a paraffinic hydrocarbon alone or a mixture of a paraffinic hydrocarbon with an organic solvent.

8. The process according to claim 1, wherein the paraffinic hydrocarbon has 10 or more carbon atoms.

9. The process according to claim 1, wherein the paraffinic hydrocarbon is a polymerized butene oil.

10. A process according to claim 1, wherein the phenoxyalkylamine salt of the formula [I] is a product obtained by reacting a phenol compound of the formula,

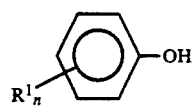

wherein $R^1$ is a $C_1$–$C_4$ alkyl group, and n is an integer of 0 to 5,
with an aziridine compound of the formula,

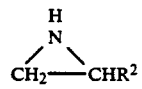

wherein $R^2$ is a $C_1$–$C_4$ alkyl group,
under elevated pressure at a temperature of 100° C. to 250° C., thereby to prepare a phenoxyalkylamine of the formula [Ia],

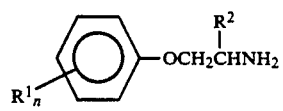
[Ia]

wherein $R^1$, $R^2$ and n are as defined above,
and reacting the above phenoxyalkylamine with hydrogen halide.

11. The process according to claim 1, wherein the phenoxyalkylamine salt of the formula (I) is a product obtained by reacting ammonia with 1-alkyl-2-phenoxyethanol of the formula,

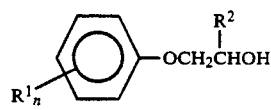

wherein each of $R^1$ and $R^2$ is, independently of other, a $C_1$–$C_4$ alkyl group, and n is an integer of 0 to 5.
in the presence of a copper-chromium catalyst and hydrogen, thereby to prepare a phenoxyalkylamine of the formula (Ia),

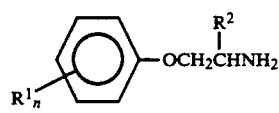
(Ia)

wherein $R^1$, $R^2$ and n are as defined above,
and reacting the above phenoxyalkylamine with hydrogen halide.

12. A process according to claim 1, wherein the phenoxyalkylamine salt of the formula [I] is a product obtained by reacting ammonia with a phenoxyalkyl halide of the formula,

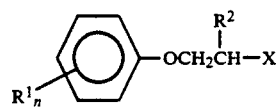

wherein each of $R^1$ and $R^2$ is, independently of other, a $C_1$-$C_4$ alkyl group, X is a halogen atom and n is an integer of 0 to 5,
thereby to prepare a phenoxyalkylamine of the formula [Ia],

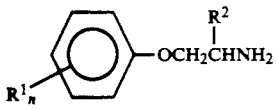

wherein $R^1$, $R^2$ and n are as defined above,
and reacting the above phenoxyalkylamine with hydrogen halide.

13. A process according to claim 1, wherein the phenoxyalkylamine salt of the formula [I] is a product obtained by subjecting a phenoxymethyl alkyl ketone of the formula,

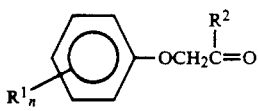

wherein each of $R^1$ and $R^2$ is, independently of other, a $C_1$-$C_4$ alkyl group, and n is an integer of 0 to 5, to reductive amination in a hydrous alcohol in the presence of a Raney nickel catalyst, thereby to prepare a phenoxyalkylamine of the formula [Ia],

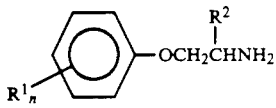

wherein $R^1$, $R^2$ and n are as defined above,
and reacting the above phenoxyalkylamine with hydrogen halide.

14. A process according to claim 1, wherein the phenoxyalkylamine salt of the formula [I] is a product obtained by reducing 1-phenoxy-2-alkanone oxime of the formula,

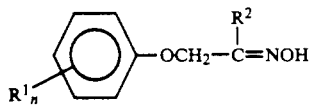

wherein each of $R^1$ and $R^2$ is, independently of other, a $C_1$-$C_4$ alkyl group, and n is an integer of 0 to 5, with hydrogen, thereby to prepare a phenoxyalkylamine of the formula [Ia],

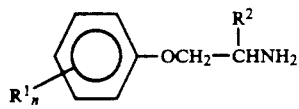

wherein $R^1$, $R^2$ and n are as defined above,
and reacting the above phenoxyalkylamine with hydrogen halide.

15. A process according to claim 1, wherein the phenoxyalkylamine salt of the formula [I] is a product obtained by reacting ammonia with 1-alkyl-2-phenoxyethyl-methanesulfonate of the formula,

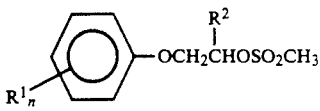

wherein each of $R^1$ and $R^2$ is, independently of other, a $C_1$-$C_4$ alkyl group, and n is an integer of 0 to 5, provided that when n is 2, there is excluded a case where one $R^1$ is substituted on the 2-position of the benzene ring and the other $R^1$ is substituted on the 6-position of the benzene ring,
thereby to prepare a phenoxyalkylamine of the formula [Ia],

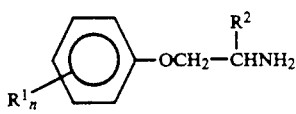

wherein $R^1$, $R^2$ and n are as defined above,
and reacting the above phenoxyalkylamine with hydrogen halide.

16. The process according to claim 1, wherein the phenoxyalkylamine salt of the formula (I) is produced by a process selected from the group selected of
(a) reacting a phenol compound of the formula,

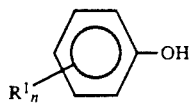

wherein $R^1$ is a $C_1$-$C_4$ alkyl group, and n is an integer of 0 to 5,
with an aziridine compound of the formula,

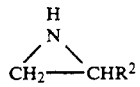

wherein $R^2$ is a $C_1$-$C_4$ alkyl group,
under elevated pressure at a temperature of 100° C. to 250° C., to prepare a phenoxyalkylamine of the formula (Ia)

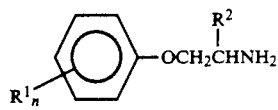

wherein $R^1$, $R^2$ and n are as defined above, and reacting said phenoxyalkylamine with a hydrogen halide;
(b) reacting ammonia with a 1-alkyl-2-phenoxyethanol of the formula

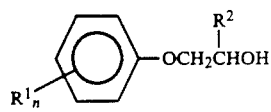

wherein each of $R^1$ and $R^2$ is, independently of the other, a $C_1$-$C_4$ alkyl group, and n is an integer of 0 to 5,
in the presence of a copper-chromium catalyst and hydrogen, to prepare said phenoxyalkylamine of the formula (Ia), and reacting said phenoxyalkylamine with a hydrogen halide;

(c) reacting ammonia with a phenoxyalkyl halide of the formula

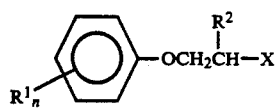

wherein each of $R^1$ and $R^2$ is, independently of the other, a $C_1$-$C_4$ alkyl group, X is a halogen atom and n is an integer of 0 to 5,
to prepare said phenoxyalkylamine of the formula (Ia), and reacting said phenoxyalkylamine with a hydrogen halide;

(d) subjecting a phenoxymethyl alkyl ketone of the formula

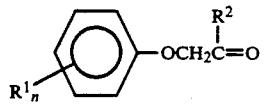

wherein each of $R^1$ and $R^2$ is, independently of the other, a $C_1$-$C_4$ alkyl group, and n is an integer of 0 to 5,
to a reductive amination with a hydrous alcohol in the presence of a Raney nickel catalyst, to prepare said phenoxyalkylamine of the formula (Ia), and reacting said phenoxyalkylamine with a hydrogen halide;

(e) reducing a 1-phenoxy-2-alkanone oxime of the formula

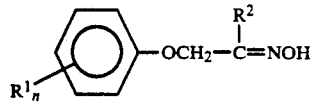

wherein each of $R^1$ and $R^2$ is, independently of the other, a $C_1$-$C_4$ alkyl group, and n is an integer of 0 to 5,
with hydrogen, to prepare said phenoxyalkylamine of the formula (Ia), and reacting said phenoxyalkylamine with a hydrogen halide; and (f) reacting ammonia with a 1-alkyl-2-phenoxyethyl-methanesulfonate of the formula

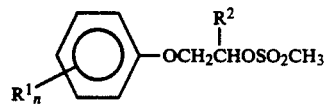

wherein each of $R^1$ and $R^2$ is, independently of the other, a $C_1$-$C_4$ alkyl group, and n is an integer of 0 to 5, provided that when n is 2, the phenoxyalkylamine where one $R^1$ is substituted on the 2-position of the benzene ring and the other $R^1$ is substituted on the 6-position of the benzene ring is excluded,
to prepare said phenoxyalkylamine of the formula (Ia), and reacting said phenoxyalkylamine with a hydrogen halide.

17. A process for producing a biguanide compound of the formula (III),

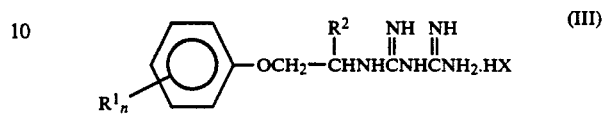

wherein each of $R^1$ and $R^2$ is, independently, a $C_1$-$C_4$ alkyl group, n is an integer of 0 to 5, and X is a halogen atom,
which comprises (a) reacting a free phenoxyalkylamine of the formula (Ia),

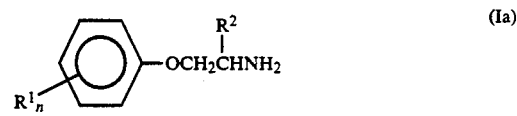

wherein $R^1$, $R^2$ and n are as defined above, with a hydrogen halide in a solvent containing a paraffinic hydrocarbon having 8 to 15 carbon atoms to prepare a phenoxyalkylamine salt of the formula (I),

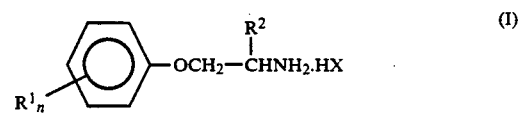

wherein $R^1$, $R^2$, n and X are as defined above,
said hydrogen halide and said phenoxyalkylamine of the formula (Ia) being in a hydrogen halide/-phenoxyalkylamine molar ratio of 1 to 3, the reaction to prepare said phenoxyalkylamine salt being carried out at a temperature of 10° C. to 50° C., and (b) reacting said phenoxyalkylamine salt with a dicyandiamide of the formula (II),

in said solvent without isolating said phenoxyalkylamine salt, said phenoxyalkylamine salt of the formula (I) and said dicyandiamide of the formula (II) being in a phenoxyalkylamine salt/dicyandiamide molar ratio of 0.5/1 to 1.5/1, and the reaction of said phenoxyalkylamine salt and said dicyandiamide being carried out at a temperature of 120° to 200° C.

18. The process according to claim 17, wherein the reaction of said free phenoxyalkylamide with said hydrogen halide and the reaction of said phenoxyalkylamide salt with said dicyandiamide are both carried out under atmospheric pressure.

19. The process according to claim 17, wherein the reaction of a free phenoxyalkylamine with said hydrogen halide and the reaction of said phenoxyalkylamine salt with said dicyandiamide are both carried out under elevated pressure.

20. The process according to claim 17, wherein the paraffinic hydrocarbon having 8 to 15 carbon atoms is selected from the group consisting of n-octane, n-nonane, n-decane, n-undecane, n-dodecane, n-tridecane, n-tetradecane, n-pentadecane, 2,2-dimethylhexane, 2,2,4-trimethylhexane, 5-methylnonane, 3-methylundecane, cyclooctane and n-hexylcyclohexane.

21. The process according to claim 20, wherein the hydrogen halide is selected from the group consisting of hydrogen chloride, hydrogen bromide, hydrogen fluoride and hydrogen iodide.

22. The process according to claim 17, wherein the phenoxyalkylamine salt/dicyandiamide molar ratio is 0.85/1 to 1/1.

23. The process according to claim 17, wherein the solvent containing a paraffinic hydrocarbon is a paraffinic hydrocarbon alone or a mixture of a paraffinic hydrocarbon with an organic solvent.

24. The process according to claim 17, wherein the paraffinic hydrocarbon has 10 or more carbon atoms.

25. The process according to claim 17, wherein the paraffinic hydrocarbon is a polymerized butene oil.

26. A process according to claim 17, wherein the phenoxyalkylamine of the formula [Ia] is a product obtained by reacting a phenol compound of the formula,

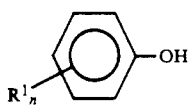

wherein $R^1$ is a $C_1$–$C_4$ alkyl group, and n is an integer of 0 to 5, with an aziridine compound of the formula,

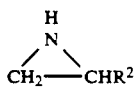

wherein $R^2$ is a $C_1$–$C_4$ alkyl group, under elevated pressure at a temperature of 100° C. to 250° C.

27. The process according to claim 17, wherein the phenoxyalkylamine of the formula (Ia) is a product obtained by reacting ammonia with 1-alkyl-2-phenoxyethanol of the formula,

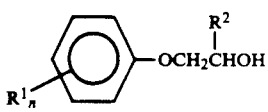

wherein each of $R^1$ and $R^2$ is, independently of other, a $C_1$–$C_4$ alkyl group, and n is an integer of 0 to 5, in the presence of a copper-chromium catalyst and hydrogen.

28. A process according to claim 17, wherein the phenoxyalkylamine of the formula [Ia] is a product obtained by reacting ammonia with a phenoxyalkyl halide of the formula,

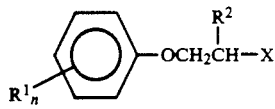

wherein each of $R^1$ and $R^2$ is, independently of other, a $C_1$–$C_4$ alkyl group, X is a halogen atom and n is an integer of 0 to 5.

29. A process according to claim 17, wherein the phenoxyalkylamine of the formula [Ia] is a product obtained by subjecting a phenoxymethyl alkyl ketone of the formula,

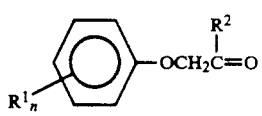

wherein each of $R^1$ and $R^2$ is, independently of other, a $C_1$–$C_4$ alkyl group, and n is an integer of 0 to 5, to reductive amination in a hydrous alcohol in the presence of a Raney nickel catalyst.

30. A process according to claim 17, wherein the phenoxyalkylamine of the formula [Ia] is a product obtained by reducing 1-phenoxy-2-alkanone oxime of the formula,

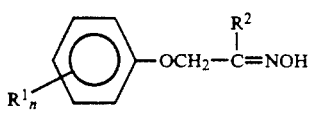

wherein each of $R^1$ and $R^2$ is, independently of other, a $C_1$–$C_4$ alkyl group, and n is an integer of 0 to 5, with hydrogen.

31. A process according to claim 17, wherein the phenoxyalkylamine of the formula [Ia] is a product obtained by reacting ammonia with 1-alkyl-2-phenoxyethylmethanesulfonate of the formula,

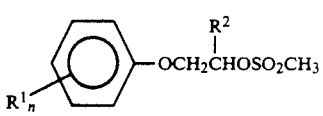

wherein each of $R^1$ and $R^2$ is, independently of other, a $C_1$–$C_4$ alkyl group, and n is an integer of 0 to 5, provided that when n is 2, there is excluded a case where one $R^1$ is substituted on the 2-position of the benzene ring and the other $R^1$ is substituted on the 6-position of the benzene ring.

32. The process according to claim 17, wherein the phenoxyalkylamine of the formula (Ia) is produced by a process selected from the group consisting of (a) reacting a phenol compound of the formula

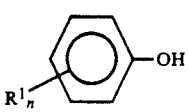

wherein $R^1$ is a $C_1$–$C_4$ alkyl group, and n is an integer of 0 to 5, with an aziridine compound of the formula

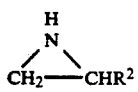

wherein $R^2$ is a $C_1$-$C_4$ alkyl group,
under elevated pressure at a temperature of 100° C. to 250° C.;

(b) reacting ammonia with 1-alkyl-2-phenoxyethanol of the formula

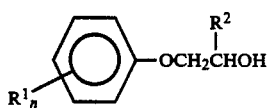

wherein each of $R^1$ and $R^2$ is, independently of the other, a $C_1$-$C_4$ alkyl group, and n is an integer of 0 to 5, in the presence of a copper-chromium catalyst and hydrogen;

(c) reacting ammonia with a phenoxyalkyl halide of the formula

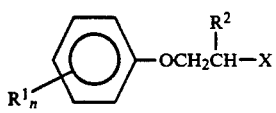

wherein each of $R^1$ and $R^2$ is, independently of other, a $C_1$-$C_4$ alkyl group, X is a halogen atom and n is an integer of 0 to 5;

(d) subjecting a phenoxymethyl alkyl ketone of the formula

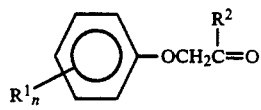

wherein each of $R^1$ and $R^2$ is, independently of the other, a $C_1$-$C_4$ alkyl group, and n is an integer of 0 to 5,
to a reductive amination in a hydrous alcohol in the presence of a Raney nickel catalyst;

(e) reducing a 1-phenoxy-2-alkanone oxime of the formula,

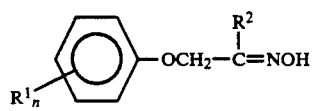

wherein each of $R^1$ and $R^2$ is, independently of the other, a $C_1$-$C_4$ alkyl group, and n is an integer of 0 to 5,
with hydrogen; and (f) reacting ammonia with a 1-alkyl-2-phenoxyethylmethanesulfonate of the formula

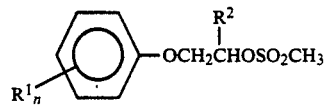

wherein each of $R^1$ and $R^2$ is, independently of other, a $C_1$-$C_4$ alkyl group, and n is an integer of 0 to 5, provided that when n is 2, the phenoxyalkylamine where one $R^1$ is substituted on the 2-position of the benzene ring and the other $R^1$ is substituted on the 6-position of the benzene ring is excluded.

* * * * *

UNITED STATES PATENT AND TRADEMARK OFFICE
CERTIFICATE OF CORRECTION

PATENT NO. : 5,286,905
DATED : February 15, 1994
INVENTOR(S) : NAKAMURA et al It is certified that error appears in the above-identified patent and that said Letters Patent is hereby corrected as shown below:

On the title page, Item: [75] Inventors:
delete "Hidetoshi Koga".

Signed and Sealed this

Eighteenth Day of June, 1996

*Attest:*

BRUCE LEHMAN

*Attesting Officer*     *Commissioner of Patents and Trademarks*